United States Patent [19]

Sintov et al.

[11] Patent Number: 5,585,379
[45] Date of Patent: Dec. 17, 1996

[54] ACYCLOVIR ANTIVIRAL GEL COMPOSITION

[75] Inventors: Amnon Sintov, Omer; Rina Uzan, Beer Sheva, both of Israel

[73] Assignee: AGIS Industries (1983) Ltd., Yerucham, Israel

[21] Appl. No.: 186,259

[22] Filed: Dec. 28, 1993

[30] Foreign Application Priority Data

Dec. 30, 1992 [IL] Israel ....................................... 104283

[51] Int. Cl.$^6$ ................................... A61K 31/52
[52] U.S. Cl. .................... 514/262; 514/944; 514/946; 514/947; 424/677
[58] Field of Search ................. 514/49, 50, 256, 514/261, 944, 946; 424/677

[56] References Cited

U.S. PATENT DOCUMENTS

| | | | |
|---|---|---|---|
| 4,537,776 | 8/1985 | Cooper | 514/825 |
| 4,956,184 | 9/1990 | Kross | 514/931 |

FOREIGN PATENT DOCUMENTS

| | | | |
|---|---|---|---|
| 0135312A2 | 3/1985 | European Pat. Off. | 514/50 |
| 0397211A2 | 11/1990 | European Pat. Off. | 514/50 |

OTHER PUBLICATIONS

Toshinobu Seki et al., *Enchanced Transdermal Delivery of Zidovudine in Rats and Human Skin*, Chem. Pharm. Bull., vol. 38, No. 11, 1990 (pp. 3086–3089).

Toshinobu Seki et al., *Percutaneous Absorption of Azidothyumidine in Rats*, International Journal of Pharmaceutics, vol. 57, 1989 (pp. 73–75).

*Primary Examiner*—James O. Wilson
*Attorney, Agent, or Firm*—Darby & Darby

[57] ABSTRACT

An antiviral topical pharmaceutical composition for treating viral diseases of the skin or mucosa comprises a poorly soluble antiviral nucleoside derivative, dispersed in an aqueous gel carrier containing a gelling agent and a water-soluble carboxylic or dicarboxylic acid salt.

1 Claim, 6 Drawing Sheets

ACYCLOVIR ANTIVIRAL GEL COMPOSITION

The present invention relates to an antiviral topical pharmaceutical composition.

More particularly, the present invention relates to a topical pharmaceutical composition containing a water-insoluble, antiviral nucleoside derivative dispersed in an aqueous gel carrier.

Many antiviral nucleoside derivatives are known, which suffer from the problem of low solubility in water and almost total insolubility in hydrophobic systems. The antiviral nucleoside derivatives that are sparingly soluble in water include:

1. Acyclovir [9-(2-hydroxyethoxymethyl)quanine]
2. Vidarabine (adenine arabinoside)
3. Azidothymidine (AZT, Retrovir, Zidovudine, 3(-azido-3'-deoxythymidine
4. Ganciclovir [9-(1,3-dihydroxy-2-propoxy)methylguanine, DHPG]

An especially important antiviral nucleoside derivative is acyclovir.

As described and explained in Israel Patent 63351:

"Acyclovir and pharmaceutically acceptable salts and esters thereof are known to have antiviral activity against various classes of DNA and RNA viruses, both in vitro and in vivo, see UK Patent No. 1,523,865 (corresponding to Israel Patent 48035). In particular, the compound is active against herpes simplex virus, which causes herpetic keratitis in rabbits, herpetic encephalitis in mice, and cutaneous herpes in guinea pigs.

"Acyclovir suffers from the disadvantage that it has a low solubility in water and is almost totally insoluble in hydrophobic solvent systems. It is accordingly difficult to produce a topical formulation containing a sufficiently dissolved concentration of active ingredient for it to exert its full effect and also to optimise the flux of the compound into the skin. In addition to ease of release, it is also important that any formulation of a pharmaceutically active compound should be stable for long periods of time; should not lose its potency; should not discolour or form insoluble substances or complexes; and also should not be unduly irritating to the skin or mucosa."

Said patent teaches solving the above stated problem by providing an oil-in-water topical pharmaceutical formulation for treating virus diseases of the skin or mucosa, of 9-(2-hydroxyethoxymethyl)guanine (hereinafter referred to as acyclovir) or a pharmaceutically acceptable salt and ester thereof, having a dispersed oil phase and a continuous aqueous phase, characterised in that the aqueous phase comprises water, at least 30% w/w of a water-miscible polyhydric alcohol and solubilized acyclovir or salt or ester thereof.

The present invention comes to challenge the accepted practice relating to penetration of acyclovir and other nucleoside analogues through biological membranes, using a different drug vehicle/dosage form.

As stated, acyclovir is a guanosine analogue with potent antiviral activity against herpes simplex virus. This agent is a prescription antiviral agent, currently marketed by Burroughs-Wellcome under the trade name ZOVIRAX®, and is available for topical use as 5% (w/w) ointment or cream in a polyethylene glycol base.

The ability to deliver acyclovir to herpes simplex virus infections is a prerequisite of any dosage form developed. There are a considerable amount of reports pointing out that topical acyclovir therapy lacks efficacy as compared to oral or parenteral administrations. The lack of efficacy can most likely be related to the poor water-solubility and lipophilicity of acyclovir, resulting in its inadequate skin or mucous membrane partitioning ability.

The present invention relates to a novel composition consisting of poorly water-soluble active ingredients in a gel formulation. Although this composition is an aqueous gel, it enhances the absorption of acyclovir and its related lipophilic compounds to the skin and through the skin, as well as mucous membranes of the nasal, buccal, sublingual and vaginal cavities. It is noteworthy that the delivery of drugs through the skin or mucous membranes offers a targeting of the drugs in a local manner to the affected area, accompanying a significant reduction in side effects and drug biodegradation.

Thus, according to the present invention there is now provided an antiviral, topical pharmaceutical composition for treating viral diseases of the skin or mucosa, comprising a poorly water-soluble, antiviral nucleoside derivative dispersed in an aqueous gel carrier containing a gelling agent and a carboxylic or dicarboxylic acid salt, such as a water solubilized $C_{16}$–$C_{18}$ carboxylic acid salt, e.g., a linoleate, elaidate, palmitate, myristate or oleate, or a dicarboxylic acid salt, e.g., a malonate, succinate, adipate, pimelate, maleate, fumerate or azelate.

Said compositions can further comprise a carboxylic or dicarboxylic acid in combination with said acid salt.

In contradistinction to the approaches suggested in the prior art of utilizing water-in-oil or oil-in-water emulsions in an ointment or cream topical delivery system, it has now been found, according to the present invention, that a gel formulation containing a soluble salt of a carboxylic or dicarboxylic acid, such as sodium or potassium oleate, enhances the permeation of a poorly absorbed drug (e.g., acyclovir) through skin. A composition consisting of potassium oleate is superior over an o/w or w/o cream. As shown in the examples hereinafter, ZOVIRAX (o/w) cream delivers more drug than w/o cream. However, a continuous aqueous phase gel functions as an even more effective drug delivery system when water-soluble carboxylic or dicarboxylic acid salt is included therein. Therefore, the present invention in its preferred embodiment provides an enhanced bioavailability of acyclovir and its poorly absorbed derivatives, and provides an unexpectable improved delivery of acyclovir from an aqueous dosage form to and through the skin and other mucous membranes, thus increasing the blood level of the active agent.

Thus the present invention, in especially preferred embodiments, provides a topical pharmaceutical composition comprising an antiviral topical aqueous gel pharmaceutical composition according to the present invention, comprising 0.1–30% of an alkali oleate, 0.5–20% acyclovir, 0–70% propylene glycol, 0–50% glycerine and 0.1–5% of a gelling agent.

Preferably, said antiviral topical aqueous gel pharamaceutical composition will also comprise a polyhydroxy compound of the type known in the art such as glycerine, propylene glycol and polyethylene glycol.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

In the following examples and comparative examples, tradenames and/or trademarks will be used to indicate components of compositions instead of the chemical names, according to the following key:
1. NIPAGIN™—ethylparaben, 4-hydroxybenzoic acid ethyl ester
2. NAPASOL™—propylparaben, 4-hydroxybenzoic acid propyl ester
3. CARBOPOL™ 940—carbomer, carboxyvinyl polymer, carboxypolymethylene
4. LUTROL ™ F-127—poloxamer 407, polyethylenepolypropylene glycols
5. METHOCEL K 15M—Hydroxypropyl methylcellulose
6. TRANSCUTOL™—ethoxy di-glycol
7. DRAGOSAN™ W/O—a mixture of sorbitan isostearate, hydrogenated castor oil, ceresin, beeswax and mineral oil
8. VESTAN™ 50—mineral oil
9. MYGLOIL™ 812—caprylic/capric acids
10. DRAGOXAT™ EH—octyldodecyl octanoate

COMPARATIVE EXAMPLE 1 a) The objective of the present study was to compare several acyclovir gels and one w/o cream that were formulated in our laboratory with 5% ZOVIRAX (o/w) cream (Burroughs-Wellcome, North Carolina), in their ability to deliver the drug transdermally. The gels and the w/o cream were physically acceptable as topical preparations and could challenge the present patents, if they would deliver the drug effectively. That was, basically, the goal of the present study.

b) The formulations were prepared and sent to an independent laboratory for transdermal assessment in two separated experiments. The first experiment was performed with formulations designated AGD2110, AGD2210, AGD21T10, AGD22T10 and a commercial ZOVIRAX cream (D8289). All these formulations were radiolabeled under gentle heating with 0.04 mCi of tritiated acyclovir per 5g of the gel. The second experiment was conducted with formulations designated AGD37, AGD38A, ZOVIRAX and ACD03. All preparations were tested for acyclovir permeation through hairless rat skin in a diffusion cell system. The permeated acyclovir was analyzed in the first experiment by measuring the radioactivity (in dpm/mg), and in the second experiment by HPLC. Only product ACD03, from which a 5 g specimen was taken and radiolabeled (without heating), was analyzed by the two methods.

c. Formulations:

| | Conc., % | | | | | |
|---|---|---|---|---|---|---|
| | AGD | | | | | |
| Ingredients | 21A (2110) | 22A (2210) | 21A-3 (21T10) | 22A-3 (22T10) | 37 | 38A |
| Acyclovir mic.** | 5 | 5 | 5 | 5 | 5.3* | 5.3* |
| Purified Water | 60 | 66.6 | 55 | 61.6 | 35 | 45.3 |
| Propyl. Glycol | 25 | — | 20 | — | 39.5 | 38 |
| Nipagin | 0.2 | 0.2 | 0.2 | 0.2 | 0.2 | 0.1 |
| Nipasol | — | — | — | — | 0.0 | 0.0 |
| Glycerine | 6.6 | 6.6 | 6.6 | 6.6 | — | — |
| Cyclodextrine | 1.6 | — | 1.6 | — | — | — |
| Carbopol 940 | 0.8 | 0.8 | 0.8 | 0.8 | — | — |
| Lutrol F-127 | — | — | — | — | 20 | — |
| Pot. oleate 40% | — | — | — | — | — | 7 |
| Methocel-K 15M | — | — | — | — | — | 1.5 |
| citric acid 20% | — | — | — | — | — | 2.7 |
| NaOH 20% | 0.8 | 0.8 | 0.8 | 0.8 | — | — |
| Transcutol | — | — | 10 | 10 | — | — |
| Alcohol (ethanol) | — | 20 | — | 15 | — | — |

| Ingredients | ACD 03 |
|---|---|
| Phase A: | |
| Dragosan w/o | 8 |
| Vestan-50 | 6 |
| Mygloil-812 | 10 |
| Dragoxat EH | 4 |
| Nipasol | 0.0 |
| Phase B: | |
| Acyclovir mic. | 0.5 |
| Purified water | 63 |
| MgSO₄.7H₂O | 0.7 |
| Propyl. glycol | 3 |
| Nipagin | 0.1 |
| Phase C: | |
| Acyclovir mic | 4.7 |

*A correction was made in accordance to the material's assay.
**Resfar R-51209-021 d) Manufacturing Procedure:

Formulations containing glycerine were prepared by dispersing acyclovir in the glycerine, and mixing this paste with an aqueous solution of the other ingredients. Small portions of acyclovir (16%) were dissolved in the aqueous solution by using an appropriate amount of sodium hydroxide. The last step was an addition of carbopol and mixing until an homogeneous gel was obtained.

Formulation AGD37 and AGD38A were prepared by dispersing the acyclovir in propylene glycol (and potassium oleate as in AGD38A). Then, the aqueous solution containing the preservative was added and mixed followed by a subsequent addition of the gelling agent. The pH was adjusted, if necessary, to 7–8.

The w/o cream (ACD03) was prepared as follows:
1. Phase A was heated while stirring at 80° C.
2. Phase B was prepared by dissolving nipagin and magnesium sulphate in the 80° C. preheated water. While stirring, propylene glycol and the small portion of acyclovir were added and dissolved.
3. At 80° C. phase B was emulsified in phase A.
4. On cooling to 50° C., the acyclovir (phase C) was added, mixed and the cream was homogenized.

e) In-vitro Skin Permeability of Acyclovir:
Diffusion cells: The permeability of hairless rat skin to acyclovir was measured in vitro using diffusion cells. The diffusion area was 2.54 cm², and the donor compartment volume was 8 ml. The solutions in the donor side were stirred by externally driven, teflon-coated magnetic bars. Half of the cells were immersed in a 37° C.-water bath for the whole experiment. In the first experiment, 6 diffusion cells were used for each formulation, while in the second experiment only 3 were employed.

Skin preparation: Full-thickness hairless rat (5–6 wks nude rats, Hyfac Credo, Orleans, France) skin was excised from the fresh carcasses of animals (abdominal side only) sacrificed with chloroform. Subcutaneous fat was removed with a scalpel and the skin was mounted in diffusion cells. The abdominal skin of each animal was placed with the stratum corneum facing up, and five donor chambers were attached by adhering their edges using cyanoacrylate glue. The excess skin was trimmed off and the receiver chamber, defined as the side facing the dermis, was connected and filled with purified water.

Permeation: After 4 hours of the skin hydration performed at 37° C. in a water bath, the water was removed from the cells. Cream or gel specimens (100–200 mg) were accurately weighed on the skin in the donor compartments, and phosphate buffer (0.05M, pH=7.4) containing penicillin/streptomycin (Sigma. 10 ml sol./1 liter) was filled in the received sides. Cells used for the radiolabeled preparations were filled with purified water containing penicillin/streptomycin and 0.5% human serum albumin (Sigma). Samples (2 ml) were withdrawn from the receiver solution at predetermined time intervals and the cells were replenished to 8 ml with a fresh solution. The careful addition of solution into the receiver compartment took place in order to avoid air trapping beneath the dermis.

f) Calculations:

As the result of large-volume sampling from the receiver solution and replacing with equal volumes, the solution was constantly diluted. Taking this into account, cumulative drug permeation ($Q_t$) was calculated from the following equation:

$$Q_t = V_r C_t + \sum_{i=0}^{t-1} V_s C_i$$

where $C_t$ is the drug concentration of the receiver solution at each sampling time point, $C_i$ is the drug concentration of the i-th sample, $V_r$ and $V_s$ are the volumes of the receiver solution (ml) and the sample (2 ml), respectively. Data was expressed as the cumulative acyclovir permeation per unit of skin surface area, $Q_t/S$ (S=2.54 cm$^2$).

g) Analytical Techniques:

Analysis of tritium-labeled acyclovir: Specific activity and consistency of the radiolabeled drug in formulations were first checked by serial sampling (200 mg×5) and measurement of radioactivity in a liquid scintillation counter. Each one of the samples taken from the receiver chambers were divided into two specimens of about 1 ml which were accurately weighed in the scintillation vials. Then, vials were filled with scintillation liquid and radioactivity in dpm was counted.

Acyclovir concentration (mg/g solution) in the receiver chamber at each sampling point ($C_t$) was calculated as follows:

$$C_t(mg/g) = \left[ \frac{A_1}{W_1} + \frac{A_2}{W_2} \right] :2:SpA$$

where: $A_1$ and $A_2$ are the counts (in dpm) of each 1-ml specimen, and $W_1$ and $W_2$ are the weights in g of the specimens. The specific activity (SPA) of the active principal is expressed as the dpm counts of 1 mg of acyclovir in a homogeneous formulation. Tables I(a–f) present the calculation of the specific activity values of radiolabeled formulation.

HPLC analysis of acylovir: 40 μl of phosphoric acid were added into vials containing the 2-ml samples, and the mixtures were vortexed. Aliquots of 20 μl from each vial were injected into the HPLC system (Waters Model 501, Milford, Mass., U.S.A.), which was equipped with a prepared $C_{18}$ column (Lichrospher 60 RP-select B, 5 μm, 125×4mm). The detection of acyclovir was carried out at 254 nm with Waters 484 variable wavelength detector. Data was recorded on a Waters 740 Data Module single-channel integrator. The samples were chromatographed using an isocratic mobile phase consisting of a phosphate buffer (0.05M Na$_2$HPO$_4$, pH=2.5 adjusted with phosphoric acid). A flow rate of 1.3 ml/min was used. The data was analyzed using an eight-point calibration curve which was run for every series of chromatographed samples. Plots of the calibration curves [peak area versus drug concentration] over the range 1–40 μg/ml were linear (r=0.998). The lower limit of detection was 10 ng per injection.

h) Results:

Tables 2–6 represent the results of the first experiment. It is clear from this data that ZOVIRAX cream was superior to these gel formulations. After 50 hours, all gels released to the receiver solution very low amounts of acyclovir (10–40 μg/cm$^2$, while ZOVIRAX delivered 510 μg/cm$^2$). ZOVIRAX cream, however, demonstrated an unusual nonlinear permeation profile, that was repeated and confirmed further on Tables 6 (Radioactivity) and 8 (HPLC analysis).

Table 2 shows the permeation profile of the acyclovir-containing w/o cream. As mentioned above, this work was done separately from the other radiolabeled formulations. A difference between the results of the in vitro test obtained from ZOVIRAX and the w/o cream was noted after 24 hours. It should be noted that results from the radiolabeled ZOVIRAX cream were achieved about 3 months prior to the labeled w/o cream. Furthermore, the methods of dispersing the tritium-labeled acyclovir in the two cream products were different, and might have determined if tritiated acyclovir did reflect the "cold" drug release.

Since it was not clear if the radioactivity method was reliable enough, an HPLC method was also carried out. Tables 8 and 9 present the significant difference between the ZOVIRAX cream and the w/o cream in delivering acyclovir, and reflect the inaccuracy of the radiolabeling techniques. According to the data achieved by the HPLC method, ZOVIRAX o/w cream is superior as a topical drug delivery system to the w/o cream, but is comparable to the gel formulation AGD38A and even inferior (see Tables 8, 11 and 12).

As already mentioned and as it is shown in Tables 8 and 11, the permeation profile of the acyclovir demonstrated by ZOVIRAX cream was found to be nonlinear—an unusual and undesired phenomenon. Usually, it takes 4 to 6 hours for many drugs to reach a steady state flux after the onset of the system application on the surface of the skin. This lag-time is actually the time needed for drug to diffuse across the stratum corneum barrier. When the delivery sysem is removed (i.e., wiping or washing), appreciate amount of drug molecules may remain in the stratum corneum and cause a reservoir effect for many hours after the medication. With regard to the ZOVIRAX cream, the steady state flux is not reached and the reservoir effect may not exist, if the cream is incidently wiped. Therefore, skin application of ZOVIRAX cream might not be as good as the proposed gel AGD38A, which demonstrated higher in vitro acyclovir permeation after a short lag-time with a constant drug delivery rate.

i) Conclusion:

1. The incorporation of potassium oleate in gel formulation AGD38A, significantly affected the skin permeability to acyclovir.
2. ZOVIRAX cream, which was used as a reference product in these experiments, proved to deliver the drug transdermally much better than all formulations tested except the oleate-containing gel. The oleate-containing gel (AGD38A) demonstrated a constant flux of acyclovir and an enhanced skin penetration.

EXAMPLES 2–8

The following preferred compositions are prepared according to the present invention.

| Ingredient | 2 | 3 | 4 | 5 | 6 | 7 | 8 |
|---|---|---|---|---|---|---|---|
| Acyclovir | 5.0 | 5.0 | 5.0 | 5.0 | 5.0 | 5.0 | 5.0 |
| Sodium Oleate | 3.0 | 3.0 | 3.0 | 3.0 | 5.0 | 10.0 | 30.0 |
| Methocel K | 1.5 | 1.5 | 1.5 | 1.5 | 1.5 | 1.5 | 1.5 |
| Nipagin | 0.1 | 0.1 | 0.1 | 0.1 | 0.1 | 0.1 | 0.1 |
| Nipasol | 0.05 | 0.05 | 0.05 | 0.05 | 0.05 | 0.05 | 0.05 |
| Glycerine | 40.0 | — | — | — | — | — | — |
| Propylene glycol | — | 40.0 | — | — | 39.0 | 37.0 | 28.0 |
| polyethyleneglycol 400 | — | — | 40.0 | — | — | — | — |
| Citric acid sol./ Purified water ad. | 100 | 100 | 100 | 100 | 100 | 100 | 100 |

TABLE 1

| DPM | WEIGHT (mg) | Specific Activity (DPM/mg) | SpA of acyclovir (DPM/mg) |
|---|---|---|---|

(a) Specific activity of gel Preoaration No AGD2110

| | | | |
|---|---|---|---|
| 965374 | 119.2 | 8099 | 161980 |
| 1032035 | 133.5 | 7731 | 154620 |
| 952399 | 122.2 | 7794 | 155880 |
| 897689 | 106.9 | 8397 | 167940 |
| 1069639 | 136.0 | 7865 | 157300 |
| | Mean = 7977 dpm/mg | | Avg.: 159544 |
| | | | S.D.: 5457 |

(b) Specific activity of gel preparation No AGD21T10

| | | | |
|---|---|---|---|
| 909327 | 107.7 | 8443 | 168860 |
| 971167 | 114.2 | 8504 | 170080 |
| 985210 | 123.5 | 7977 | 159540 |
| 1122679 | 139.5 | 8048 | 160960 |
| 919056 | 110.8 | 8295 | 165900 |
| | Mean = 8253 dpm/mg | | Avg.: 165068 |
| | | | S.D.: 4680 |

(c) Specific activity of gel preparation No AGD2210

| | | | |
|---|---|---|---|
| 1024660 | 118.6 | 7967 | 159356 |
| 892433 | 119.6 | 7461 | 149236 |
| 943178 | 128.1 | 7362 | 147256 |
| 931417 | 115.0 | 8099 | 161985 |
| 925356 | 116.7 | 7929 | 158587 |
| | Mean = 7764 dpm/mg | | Avg.: 155284 |
| | | | S.D.: 6584 |

(d) Specific activity of gel preparation No AGD22T10

| | | | |
|---|---|---|---|
| 1056319 | 125.2 | 8437 | 168741 |
| 964027 | 104.1 | 9260 | 185211 |
| 1178337 | 139.2 | 8465 | 169301 |
| 980326 | 107.5 | 9119 | 182386 |
| 1003463 | 113.3 | 8856 | 177133 |
| | Mean = 8828 dpm/mg | | Avg.: 176554 |
| | | | S.D.: 7465 |

(e) Specific activity of ZOVIRAX cream #D8289

| | | | |
|---|---|---|---|
| 1421278 | 114.5 | 13286 | 265725 |
| 1650828 | 127.7 | 12927 | 258547 |
| 1861945 | 144.7 | 12867 | 257352 |
| 1515519 | 111.2 | 13628 | 272575 |
| 1418427 | 105.8 | 13406 | 268133 |
| | Mean = 13223 dpm/mg | | Avg.: 264466 |
| | | | S.D.: 6450 |

(f) Specific activity of cream preparation No ACD03

| | | | |
|---|---|---|---|
| 2593503 | 210.3 | 12332 | 246648 |
| 2280941 | 220.6 | 10340 | 206794 |
| 1317710 | 160.9 | 8189 | 163792 |
| 1327891 | 181.6 | 7312 | 146243 |
| 1404385 | 175.9 | 7984 | 159680 |
| | Mean = 9231 dpm/mg | | Avg.: 184631 |
| | | | S.D.: 41436 |

TABLE 2

Cumulative permeated acyclovir
Gel preparation - AGD2110

| Time (h) | $Q_t$ (µg) | $Q_t/S$ (µg/cm²) | S.D (n = 6) |
|---|---|---|---|
| 1.5 | 0.000 | 0.0 | 0.0 |
| 3 | 2.794 | 1.1 | 0.3 |
| 5.5 | 5.588 | 2.2 | 0.7 |
| 6.5 | 5.664 | 2.2 | 0.7 |
| 8 | 6.350 | 2.5 | 0.8 |
| 10 | 6.858 | 2.7 | 0.8 |
| 12 | 7.366 | 2.9 | 1.0 |
| 24 | 35.560 | 14.0 | 4.0 |
| 29 | 43.180 | 17.0 | 5.2 |
| 34 | 55.880 | 22.0 | 7.0 |
| 49 | 95.504 | 37.6 | 11.0 |

Flux: 0.77 ± 0.2 µg/cm²/h
Lag time: 4.3 h

TABLE 3

Cumulative permeated acyclovir
Gel preparation - AGD2210

| Time (h) | $Q_t$ (µg) | $Q_t/S$ (µg/cm²) | S.D (n = 6) |
|---|---|---|---|
| 1.5 | 0.000 | 0.0 | 0.0 |
| 3 | 5.715 | 2.2 | 0.8 |
| 6 | 5.690 | 2.2 | 0.8 |
| 8 | 8.306 | 3.3 | 1.2 |
| 10 | 10.668 | 4.2 | 1.5 |
| 22 | 21.844 | 8.6 | 3.0 |
| 24 | 25.146 | 9.9 | 4.0 |
| 27 | 29.710 | 11.7 | 4.0 |
| 34 | 38.862 | 15.3 | 5.0 |
| 46 | 55.880 | 22.0 | 8.0 |

Flux: 0.47 ± 0.2 µg/cm²/h
Lag time: 1 h

TABLE 4

Cumulative permeated acyclovir
Gel preparation - AGD21T10

| Time (h) | $Q_t$ (µg) | $Q_t/S$ (µg/cm²) | S.D (n = 6) |
|---|---|---|---|
| 1.5 | 0.000 | 0.0 | 0.0 |
| 3 | 1.270 | 0.5 | 0.3 |
| 5.5 | 2.286 | 0.9 | 0.6 |
| 6.5 | 2.794 | 1.1 | 0.6 |
| 8 | 3.505 | 1.4 | 1.0 |
| 10 | 4.166 | 1.6 | 0.0 |
| 12 | 4.826 | 1.9 | 0.4 |
| 24 | 12.192 | 4.8 | 0.9 |
| 29 | 18.542 | 7.3 | 0.5 |
| 34 | 20.320 | 8.0 | 0.5 |
| 49 | 29.972 | 11.8 | 2.2 |

Flux: 0.25 ± 0.05 µg/cm²/h
Lag time: 2.4 h

TABLE 5

Cumulative permeated acyclovir
Gel preparation - GD22T10

| Time (h) | $Q_t$ (µg) | $Q_t/S$ (µg/cm²) | S.D (n = 6) |
|---|---|---|---|
| 1.5 | 0.000 | 0.0 | 0.0 |
| 3 | 2.794 | 1.1 | 0.5 |
| 5.5 | 5.944 | 2.3 | 1.4 |

TABLE 5-continued

Cumulative permeated acyclovir
Gel preparation - GD22T10

| Time (h) | $Q_t$ (μg) | $Q_t/S$ (μg/cm$^2$) | S.D (n = 6) |
|---|---|---|---|
| 6.5 | 5.588 | 2.2 | 1.0 |
| 8 | 5.385 | 2.1 | 1.4 |
| 10 | 7.010 | 2.7 | 0.3 |
| 12 | 8.636 | 3.9 | 2.5 |
| 24 | 26.162 | 10.3 | 3.4 |
| 29 | 34.798 | 13.7 | 3.8 |
| 34 | 39.116 | 15.4 | 4.2 |
| 49 | 61.468 | 24.2 | 7.0 |

Flux: 0.51 ± 0.2 μg/cm$^2$/h
Lag time: 2.7 h

TABLE 6

Cumulative permeated acyclovir
ZOVIRAX cream - #D8289

| Time (h) | $Q_t$ (μg) | $Q_t/S$ (μg/cm$^2$) | S.D (n = 6) |
|---|---|---|---|
| 1.5 | 0.000 | 0.0 | 0.0 |
| 3 | 5.080 | 2.0 | 1.0 |
| 5 | 38.100 | 15.0 | 6.0 |
| 6.5 | 48.260 | 19.0 | 6.0 |
| 8 | 58.420 | 23.0 | 7.0 |
| 9 | 68.420 | 27.0 | 9.0 |
| 10 | 76.200 | 30.0 | 10.0 |
| 12 | 93.980 | 37.0 | 15.0 |
| 24 | 100.500 | 75.0 | 30.0 |
| 30 | 406.400 | 160.0 | 50.0 |
| 36 | 635.000 | 250.0 | 80.0 |
| 48 | 1295.400 | 510.0 | 170.0 |

Flux: 9.4 ± 3 μg/cm$^2$/h
Lag time: 6 h

TABLE 7

Cumulative permeated acyclovir
Cream (w/o) - ACD03

| Time (h) | $Q_t$ (mg) | $Q_t/S$ (μg/cm$^2$) | S.D (n = 3) |
|---|---|---|---|
| 1.25 | 0.001 | 0.42 | 0.40 |
| 3.25 | 0.011 | 4.26 | 4.67 |
| 15.50 | 0.118 | 46.44 | 27.59 |
| 19.33 | 0.167 | 66.02 | 35.60 |
| 23.16 | 0.211 | 83.20 | 45.23 |
| 41.00 | 0.486 | 191.52 | 92.76 |

TABLE 8

Cumulative permeated acyclovir
(Results acc. to HPLC analysis)
Cream (o/w) - ZOVIRA

| Time (h) | $Q_t$ (mg) | $Q_t/S$ (μg/cm$^2$) | S.D (n = 3) |
|---|---|---|---|
| 2 | 3.16 | 1.24 | 0.10 |
| 4 | 4.53 | 1.78 | 0.53 |
| 16 | 40.09 | 15.78 | 13.82 |
| 20 | 60.47 | 23.81 | 15.32 |
| 24 | 166.68 | 65.62 | 3.80 |

TABLE 9

Cumulative permeated acyclovir
(Results acc. to HPLC analysis)
Cream (w/o) preparation - ACD03

| Time (h) | $Q_t$ (mg) | $Q_t/S$ (μg/cm$^2$) | S.D (n = 3) |
|---|---|---|---|
| 2 | 3.29 | 1.29 | 0.27 |
| 4 | 5.22 | 2.05 | 0.68 |
| 16 | 6.90 | 2.71 | 0.25 |
| 20 | 7.17 | 2.82 | 0.19 |
| 24 | 9.27 | 3.65 | 0.66 |

TABLE 10

Cumulative permeated acyclovir
(Results acc. to HPLC analysis)
Gel preparation - AGD37

| Time (h) | $Q_t$ (mg) | $Q_t/S$ (μg/cm$^2$) | S.D (n = 3) |
|---|---|---|---|
| 2 | 3.07 | 1.21 | 0.12 |
| 4 | 4.50 | 1.77 | 0.65 |
| 16 | 4.89 | 1.93 | 1.42 |
| 20 | 4.10 | 1.61 | 1.56 |
| 24 | 9.00 | 3.54 | 4.89 |

TABLE 11

Cumulative permeated acyclovir
(Results acc. to HPLC analysis)
Gel preparation - AGD38A

| Time (h) | $Q_t$ (mg) | $Q_t/S$ (μg/cm$^2$) | S.D (n = 3) |
|---|---|---|---|
| 2 | 4.47 | 1.76 | 0.37 |
| 4 | 8.28 | 3.26 | 1.55 |
| 16 | 113.75 | 44.78 | 23.48 |
| 20 | 139.50 | 54.92 | 30.48 |
| 24 | 190.41 | 74.96 | 37.92 |

TABLE 12

Cumulative PERCENT of permeated acyclovir

| Time (h) | ZOVIRAX (o/w) | ACD03 (w/o) | AGD38A (gel) |
|---|---|---|---|
| 2 | 0.036 | 0.048 | 0.060 |
| 4 | 0.054 | 0.080 | 0.111 |
| 16 | 0.526 | 0.104 | 1.520 |
| 20 | 0.768 | 0.108 | 1.870 |
| 24 | 1.906 | 0.136 | 2.550 |

Further formulation work and in vitro biological evaluation was carried out, the results of which highlight the properties of the presently claimed gel composition, and support the advantages of the invention.

In general, all formulation experiments were performed as described in Example 1 hereinabove (for gel preparations). In several preparations, a modification was made in the manufacturing procedure. Instead of using sodium oleate as the raw material, an equivalent oleic acid was added and converted "in-process" to sodium oleate by a stochiometric amount of sodium hydroxide (see formulations AGD-57, 58, 65).

The in vitro percutaneous absorption/penetration of acyclovir from the gel or cream vehicles was carried out using Franz diffusion cell system (1.767 cm² diffusion area, Crown Bioscientific, Inc., New Jersey, U.S.A.). Skin was excised from the abdominal side of nude mice (CD-1) purchased from Weitzmann Institute, Israel. In some experiments, hairless guinea pigs were used (males, IAF/HA-HO, Charles River, Va. U.S.A.).

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

The following further comparative example is to be read in conjunction with said aforementioned drawings.

COMPARATIVE EXAMPLE 9

The following further formulations were manufactured and examined:

| Ingredient | AGD-42 (RDAG-2) | AGD-46 | AGD-47 | AGD-49 | AGD-52* | AGD-53 | AGD-57 | AGD-58* | AGD-65 | RDAG-4 | RDAG-5 |
|---|---|---|---|---|---|---|---|---|---|---|---|
| Acyclovir | 5.0 | 5.0 | 5.0 | 5.0 | 5.0 | 5.0 | 5.0 | 5.0 | 5.0 | 5.0 | 5.0 |
| Sodium oleate | 5.0 | — | — | — | 5.0 | 10.0 | — | — | — | 5.0 | — |
| Oleic acid** | — | 3.0 | — | 1.0 | — | — | 4.4 | 4.4 | 4.4 | — | 4.4 |
| Methocel K-15M | 1.5 | 1.5 | 1.5 | 1.5 | 1.5 | 1.5 | 1.9 | 1.9 | 2.5 | 1.9 | 1.9 |
| Nipagin | 0.1 | 0.1 | 0.1 | 0.1 | 0.1 | 0.1 | 0.1 | 0.1 | 0.1 | 0.1 | 0.1 |
| Nipasol | 0.02 | 0.02 | 0.02 | 0.02 | 0.02 | 0.02 | 0.02 | 0.02 | 0.02 | 0.02 | 0.02 |
| Propylene glycol | 38.0 | 40.0 | 40.0 | 40.0 | 50.0 | 50.0 | so.0 | 50.0 | 50.0 | 50.0 | 50.0 |
| NaOH 10 N sol. | — | 0.67 | 1.4 | 1.1 | — | — | 0.64 | 0.64 | 0.64 | — | 0.64 |
| Citric acid 20% solution | 3.2 | 3.7 | 3.9 | 3.4 | 3.2 | 4.4 | 3.0 | 3.0 | 2.9 | 3.2 | 3.0 |
| Water, up to | 100% | 100% | 100% | 100% | 100% | 100% | 100% | 100% | 100% | 100% | 100% | pH of gel preparations ranged between 7.3–7.7.
*AGD-52 was similar to RDAG-4, except that Methocel had been increased to 1.9%.
AGD-58 was similar to RDAG-5, except that a different source of oleic acid was used.
**The source of oleic acid was Oleofina, except AGD-58 (Mallinkrodt), AGD-65 and RDAG-5 (Unichem).

Figure 1:
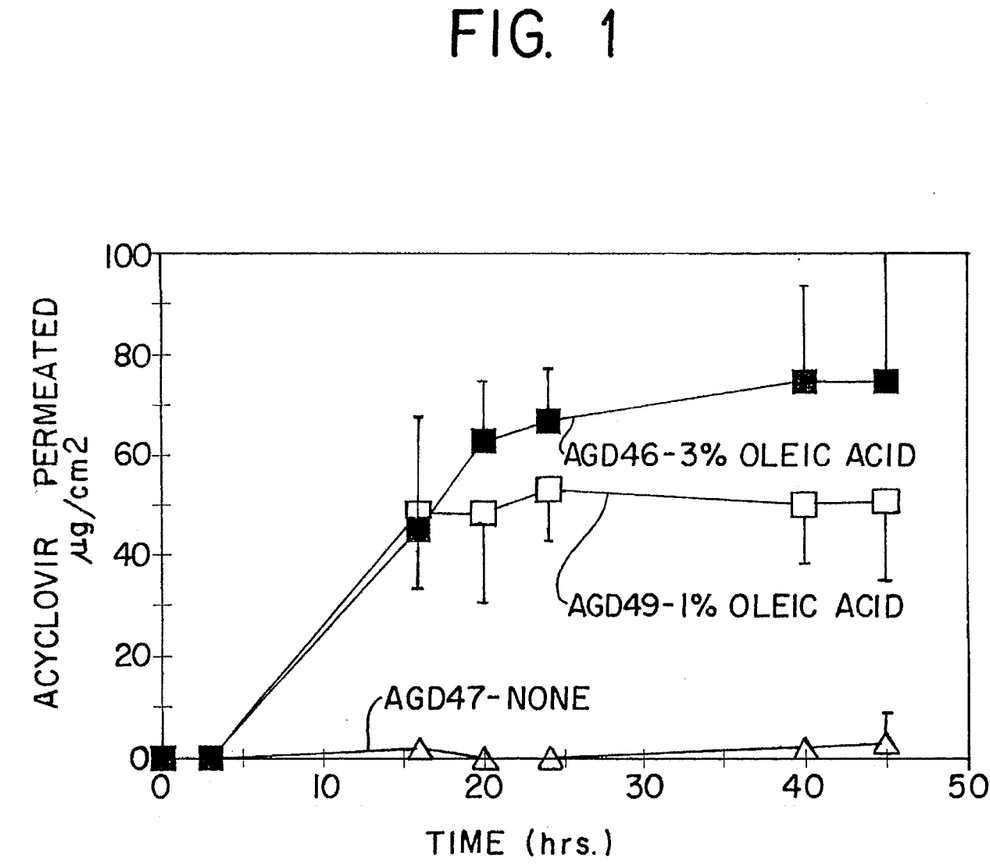
FIG. 1 is a graph of the influence of different levels of oleic acid on acyclovir penetration across guinea pig's skin.

A. Influence of the Oleic Acid and Its Concentration on Alcyclovir Permeated Amounts Formulations AGD-46, 49 and 47 were examined together and compared in two sets of in vitro permeation experiments, using guinea pigs. AGD-46 contained 3% oleic acid; AGD-49 contained 1% oleic acid; while AGD-47 contained no oleic acid but all other ingredients were identical (pH values were 7.54, 7.58 and 7.4, respectively). FIG. 1 shows the obtained penetration pattens, indicating the significance of oleic acid/sodium oleate as the penetration enhancer in the gel vehicle. Preparation with 3% oleic acid demonstrated higher permeated levels of acyclovir as compared with the preparation with 1% oleic acid. Almost no permeation was observed with the vehicle that did not contain oleic acid/oleate at all.

Figure 2:
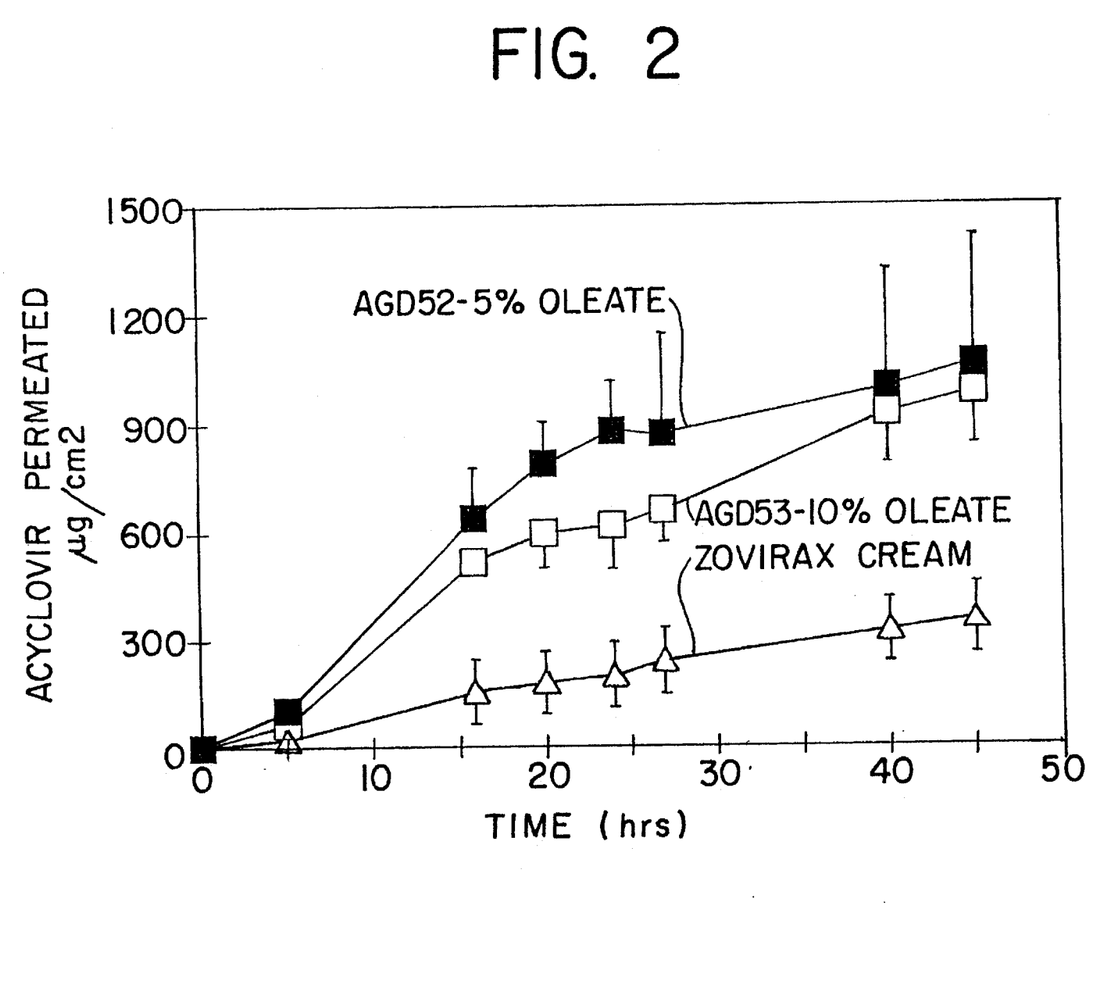
FIG. 2 is a graph of percutaneous permeation of acyclovir in nude mice after application of 2 gels prepared with sodium oleate and ZOVIRAX commercial cream.

B. Use of Sodium Oleate as the Starting Raw Material in the Formulation Procedure FIG. 2 shows the penetration patterns of two gel formulations containing 5% and 10% sodium oleate, as compared with the marketed product, ZOVIRAX cream. It has been proven again that the gel vehicle of the present invention is superior over the commercial cream. The results demonstrated that the rise in oleate level from 5% to 10% did not concomitantly increase the percutaneous permeation, but even somewhat decreased the penetration. The decrease in the amount permeated can be explained only if we can understand the mechanism by which oleic acid enhances the penetration of acyclovir. It is assumed that "oleic acid selectively perturbs the inherent lipid structure of the stratum corneum, reducing the transition temperatures and cooperativity associated with their phase properties: [*Pharm. Res.*, Vol. 7, pp. 621–627 (1990)]. The enhanced transport of drug molecules through these interfacial "defects" may require water. Therefore, increase in oleate in the gel vehicle may exceed the critical micellization concentration (CMC), resulting in less water availability in the interfacial regions of the stratum corneum. It should be noted that, although up to 30% of oleate can be formulated in practice very easily, the appearance and cosmetic properties of the gel vehicle are different from formulae containing less than 10% oleate.

C. Comparison between Formulations Containing 4.4% of Oleic Acid from Various Sources (Influence of the Material's Quality)

Figure 3:
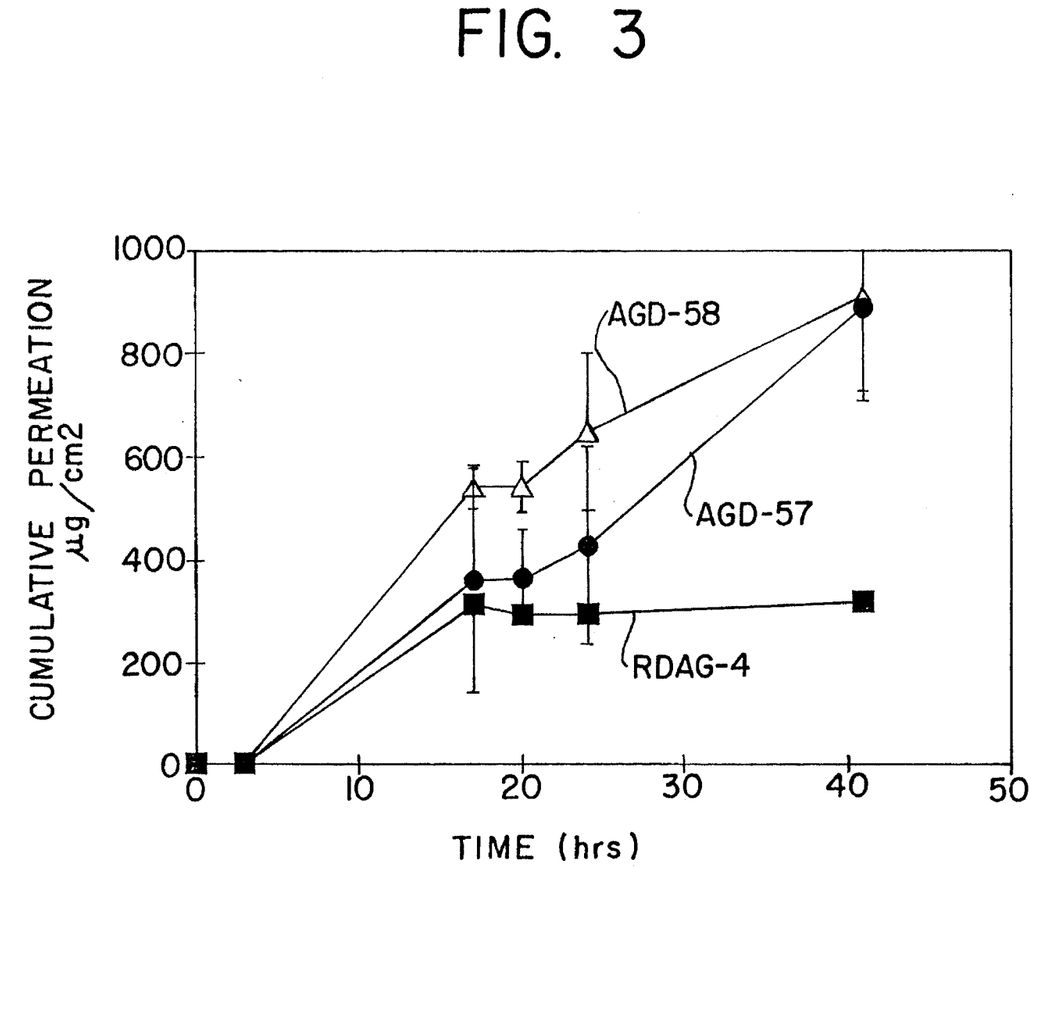
FIG. 3 is a graph of the influence of various sources of oleic acid/oleate in gel preparations.
Figure 4:
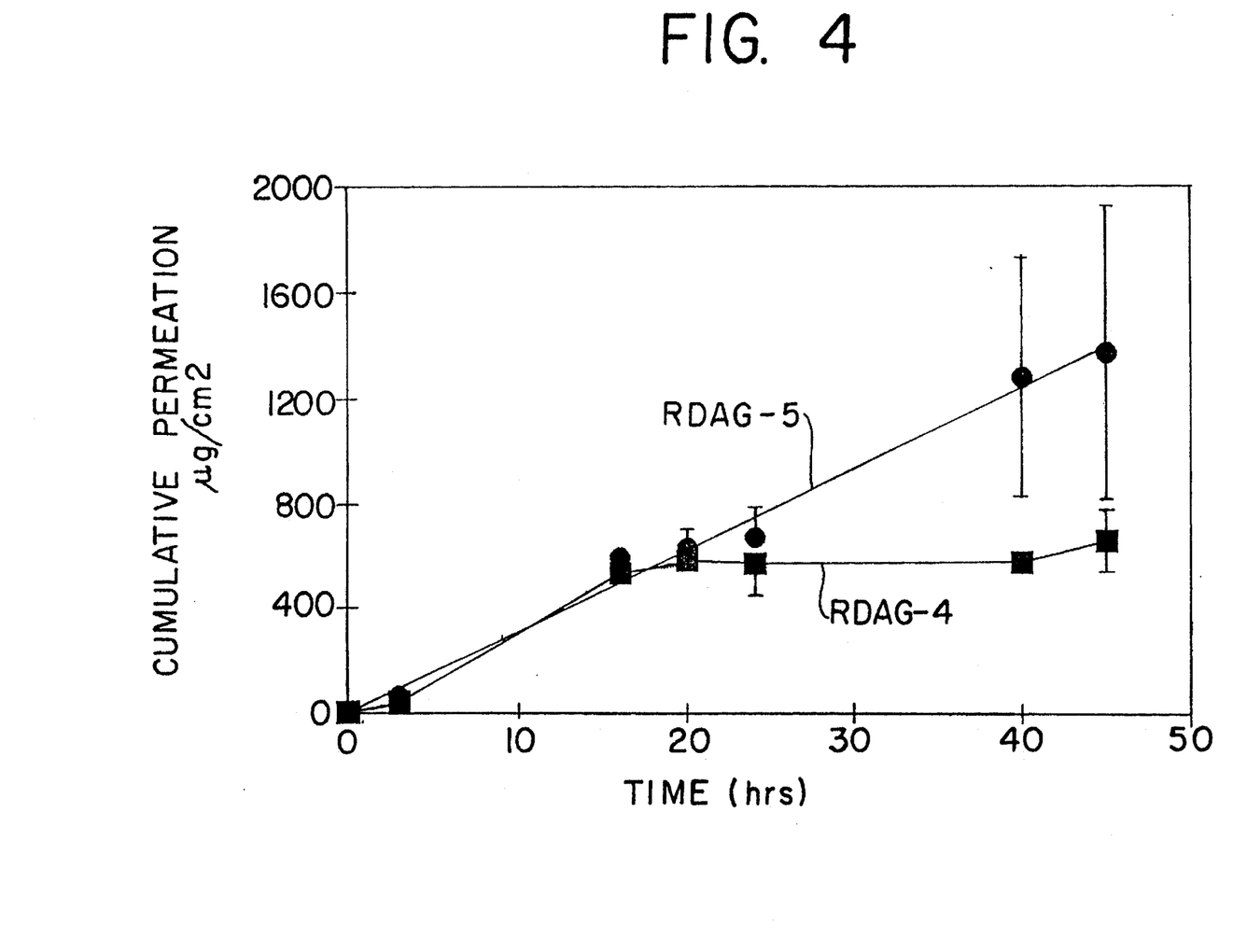
FIG. 4 is a graph of the influence of two sources of oleic acid/oleate in gel preparations.

Four sources of oleic acid were examined: Mallinckrodt, Oleofina, Unichem and Riedel-de-Haan (RDH-sod. oleate). All formulations tested were prepared with 1.9% Methocel, a change that was made to improve the consistency of the gel. FIG. 3 shows the patterns of three formulations that were tested simultaneously. From the results, Formula AGD-58, with oleic acid obtained from Mallinkrodt, had the best performance, while AGD-57 (Oleofina) had a slightly decreased flux. Formula RDAG-4 (Oleate-RDH) exhibited a poor pattern, with no more penetration after 17 hours. FIG. 4 presents the comparison between the fourth source of oleic acid—Unichem—and the already examined RDH-oleate. Here again, the differences are clear and significant, and yet all the formulations have better penetration than the Zovirax cream.

Figure 5:
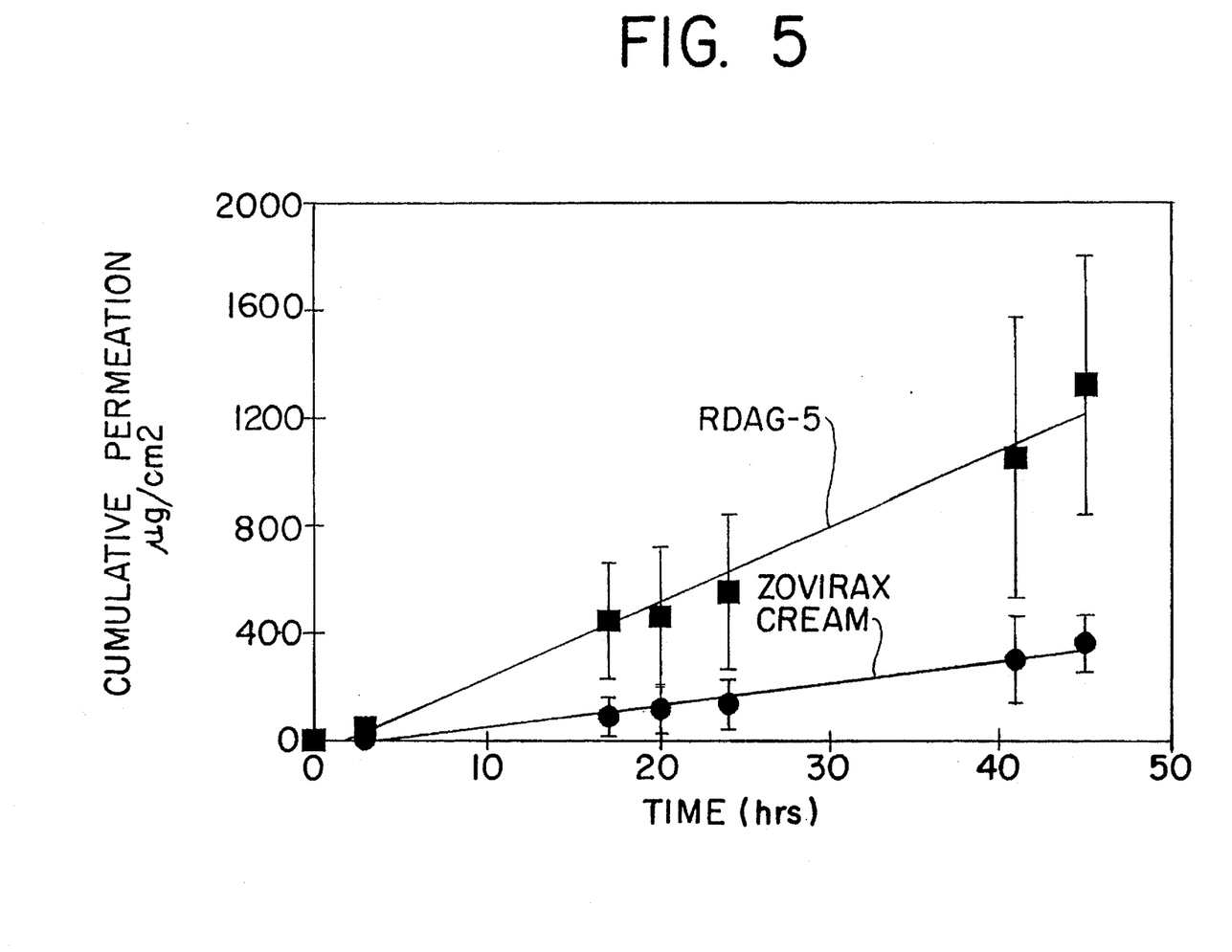
FIG. 5 is a graph of a comparison between gel RDAG-5 and ZOVIRAX commerical cream in their drug delivery (permeation across skin) profiles.
Figure 6:
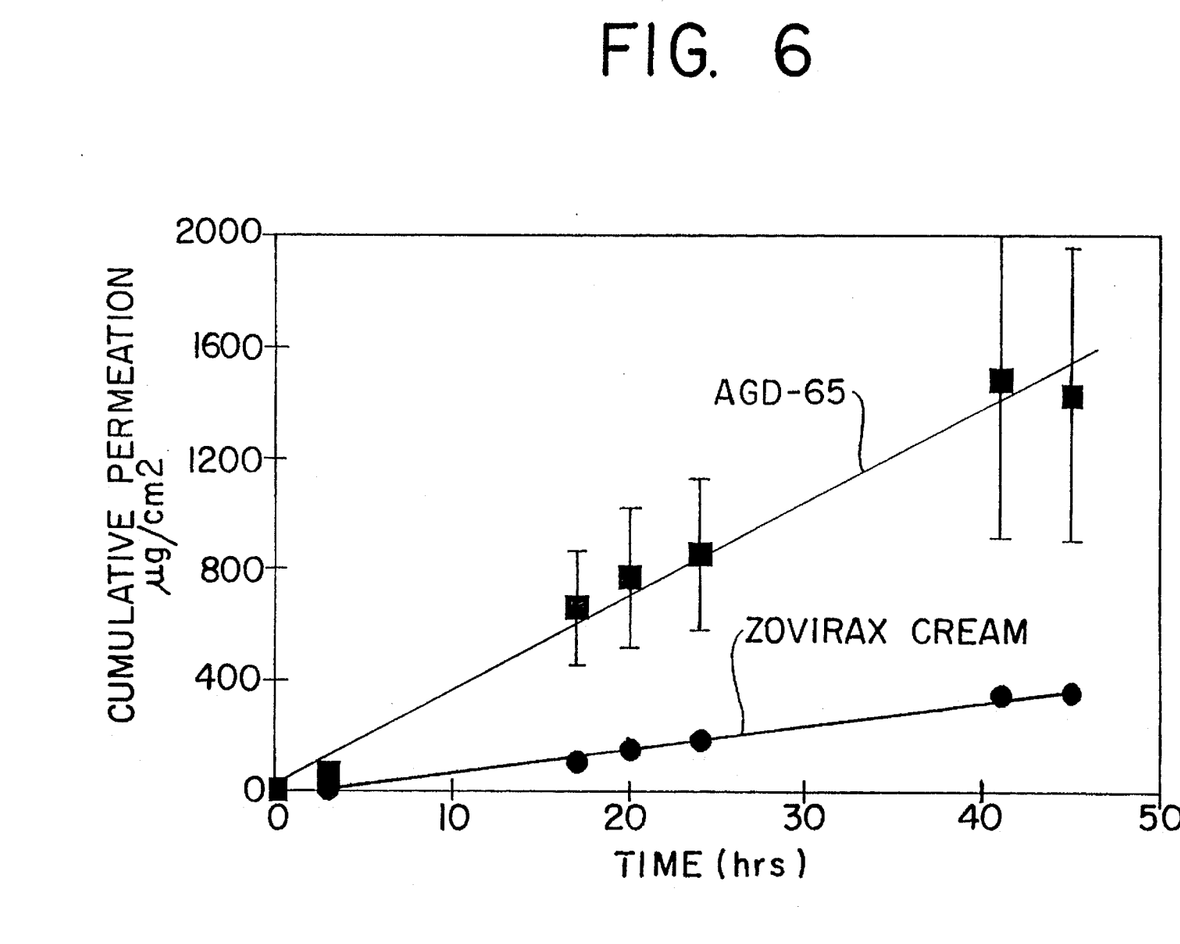
FIG. 6 is a graph of a comparison between gel AGD-65 (more Methocel K) and ZOVIRAX commercial cream in their drug delivery (permeation across skin) profiles.

D. The Validity of Results with Formulation RDAG-5 (Batch Manufactured for the Pre-Clinical Study), Influence of Methocel Addition, and Comparison with the ZOVIRAX Commerical Cream Formulation of batch RDAG-5 (corresponding to AGD-58) was reexamined in the diffusion cell system (n=6), and results overlapped those obtained previously. FIG. 5 presents these results as compared simultaneously with ZOVIRAX cream. As can be seen, the cumulative permeated amounts of acyclovir were four times higher in the gel preparation than in the commercial cream. FIG. 6 presents a comparison between a gel that contained 2.5% Methocel (instead of 1.9% in RDAG-5) and ZOVIRAX commercial cream. The results are not significantly different from those obtained previously (FIG. 5), indicating that Methocel does not affect the mechanism of penetration at this range of concentrations.

COMPARATIVE EXAMPLE 10

In-Vivo Preventive Testing of Acyclovir Gel (Formula RDAG-5) in the Topical Treatment of Experimental Cutaneous Herpes Simplex Virus Type 1 (HSV-1) Infection In a double-blind study, the efficacy of a drug-containing gel according to the present invention (batch RDAG-5) and ZOVIRAX commercial cream was evaluated as compared to a non-treatment control. A guinea pig model was selected for the cutaneous HSV-1, because the model mimics the human herpes simplex labialis infection [Hubler, et al, *J. Invest. Dermatol.*, Vol. 62, pp. 92–95 (1974)]. Forty-eight animals (young male D. Hartly guinea pig, CRL:(HA)BR strain, Charles River, Va., U.S.) were assigned to the experiment. The virus was inoculated intradermally on three locations on the back of each animal. The area into which the virus was to be inoculated was divided into three squares with a marking pen. In the middle of each area, about 20 microliters of HSV at a concentration of 106 PFU/ml was applied by 10 injections close to each other. In order to assign the location of the various treatments on each animal and to overcome any gradient effect, a latin-square design was used.

Treatment was started 2–3 hours after inoculation and consisted of three daily applications of the topical preparations (about 50 mg) for a period of three days (9 treatments). Animals were inspected once daily and the lesions (or inoculated sites) were scored in the following manner:

| Score | Description |
| --- | --- |
| 0.0 | No signs detected |
| 0.5 | Erythema and slight edema at the site |
| 1.0 | Erythema and one or two small vesicles |
| 2.0 | Erythema and numerous small vesicles |
| 2.5 | Numerous medium-sized vesicles |
| 3.0 | Numerous large vesicles |

In addition, the number of vesicles for each site was counted and recorded.

Results

Table 13 shows the mean and standard deviations of the scores, observed at day 2 and day 3 from inoculation. Table 14 presents the mean vesicle quantities at days 2 and 3, and Table 15 shows the combination of the two parameters, providing a more comprehensive picture of the diseased state. The results clearly demonstrate the significant superiority of the gel over the commercial cream and the non-treated control.

TABLE 13

Mean Score Number at Each Infection Site

| | Day 2 | Day 3 |
| --- | --- | --- |
| Control | 2.063 (± 0.727) | 1.896 (± 0.928) |
| Zovirax | 2.052 (± 0.604) | 1.833 (± 0.853) |
| ACV Gel | 2.188 (± 0.727) | 0.677 (± 0.696) |

ACV = acyclovir

TABLE 14

Mean Count of Vesicles at Each Infection Site

| | Day 2 | Day 3 |
| --- | --- | --- |
| Control | 6.167 (± 3.218) | 5.833 (± 3.328) |
| Zovirax | 5.979 (± 2.957) | 5.000 (± 3.149) |
| ACV Gel | 5.188 (± 3.057) | 0.854 (± 2.073) |

ACV = acyclovir

TABLE 15

Mean of Combined Parameters (Score X Vesicles at Each Infection Site

| | Day 2 | Day 3 |
| --- | --- | --- |
| Control | 14.479 (± 8.151) | 13.583 (± 8.118) |
| Zovirax | 13.406 (± 7.163) | 11.302 (± 7.963) |
| ACV Gel | 12.333 (± 7.563) | 1.708 (± 4.382) |

ACV = acyclovir

The gel of the present invention greatly enhances the delivery of the drug to the target site, namely, deep in skin tissues. this finding influences the efficacious administration of acyclovir for other herpes and non-herpes associated diseases. These include:

a) Post-herpetic neuralgia, which is a common cause of chronic neuropathic pain and progression of rash in the elderly population.

b) Vulvar vestibulitis in many women, who experience severe pain on vestibular touch or vaginal entry, without apparent cause. Since Friedrich [*J. Reproductive Medicine*, Vol. 33, pp. 514–518 (1988)] discovered that oral acyclovir has a therapeutic effect on vulvar vestibulitis, an efficient topical application, such as with the gel of the invention, provides more beneficial local therapy with reduced dosage and minimized adverse reactions.

c) Recurrent genital herpes.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A non-emulsion antiviral topical pharmaceutical composition comprising (a) 0.5–20%, based on 100% of said composition, of a an antiviral agent comprising acyclovir, and (b) an aqueous gel carrier comprising 0.1–30% of an alkali oleate, 0–70% propylene glycol, 0–50% glycerine and 0.1–5% of a gelling agent, based on 100% of said composition, said acyclovir being dispersed in said carrier and said gel forming a continuous phase.

* * * * *